(12) United States Patent
Voic (10) Patent No.: US 11,950,790 B2
(45) Date of Patent: Apr. 9, 2024

(54) SPINAL SURGERY METHOD AND RELATED APPARATUS

(71) Applicant: MISONIX, INCORPORATED, Farmingdale, NY (US)

(72) Inventor: Dan Voic, Cedar Grove, NJ (US)

(73) Assignee: MISONIX, LLC, Farmingdale, NY (US)

( * ) Notice: Subject to any disclaimer, the term of this patent is extended or adjusted under 35 U.S.C. 154(b) by 184 days.

(21) Appl. No.: 17/509,486

(22) Filed: Oct. 25, 2021

(65) Prior Publication Data

US 2022/0125445 A1    Apr. 28, 2022

Related U.S. Application Data

(60) Provisional application No. 63/105,331, filed on Oct. 25, 2020.

(51) Int. Cl.
| | |
|---|---|
| *A61B 17/16* | (2006.01) |
| *A61B 17/00* | (2006.01) |
| *A61B 34/30* | (2016.01) |
| *A61B 90/00* | (2016.01) |

(52) U.S. Cl.
CPC .......... *A61B 17/1671* (2013.01); *A61B 34/30* (2016.02); *A61B 90/37* (2016.02); *A61B 2017/00261* (2013.01); *A61B 2017/1648* (2013.01); *A61B 2034/301* (2016.02); *A61B 2217/005* (2013.01)

(58) Field of Classification Search
CPC ..... A61B 17/1671; A61B 34/30; A61B 90/37; A61B 2034/301; A61B 2017/00261; A61B 2017/1648; A61B 2217/005
See application file for complete search history.

(56) References Cited

U.S. PATENT DOCUMENTS

| | | | |
|---|---|---|---|
| 6,602,248 B1 * | 8/2003 | Sharps | C07D 409/12 606/41 |
| 9,603,656 B1 * | 3/2017 | Germain | A61B 17/1628 |
| 10,588,691 B2 * | 3/2020 | Pellegrino | A61B 18/18 |
| 11,672,558 B2 * | 6/2023 | Voic | A61B 17/1671 606/79 |
| 2001/0029370 A1 * | 10/2001 | Hodva | A61B 18/148 606/41 |
| 2005/0033292 A1 * | 2/2005 | Teitelbaum | A61B 17/1617 606/53 |
| 2007/0213734 A1 * | 9/2007 | Bleich | A61B 17/1671 606/79 |
| 2012/0014868 A1 | 1/2012 | Roy | |
| 2013/0103021 A1 * | 4/2013 | Germain | A61B 18/1485 606/119 |
| 2014/0350567 A1 | 11/2014 | Schmitz | |

(Continued)

*Primary Examiner* — Kevin T Truong
*Assistant Examiner* — Diana Jones
(74) *Attorney, Agent, or Firm* — R. Neil Sudol; Henry D. Coleman (57) ABSTRACT

A surgical method utilizes a surgical instrument having an elongate probe with a distal end having at least one egress or outlet port. The method comprises inserting a distal end portion of the elongate probe into a spinal disc space adjacent two spinal vertebrae, ejecting or streaming a plasma jet from the at least one egress or outlet port into spinal disc material in the spinal disc space, and subsequently removing the elongate probe from the spinal disc space.

13 Claims, 3 Drawing Sheets

(56) References Cited

U.S. PATENT DOCUMENTS

2015/0157387 A1* 6/2015 OuYang ............... A61B 1/3132
            606/34
2020/0121374 A1    4/2020 McGahan et al.

* cited by examiner

SPINAL SURGERY METHOD AND RELATED APPARATUS

BACKGROUND OF THE INVENTION

This invention relates to surgical procedures commonly known as discectomy and nucleotomy.

The spinal column comprises bones or vertebrae and also fibrous discs that are disposed between the vertebrae. The discs normally function as cushions separating the vertebrae. With age, owing to a drying of the disks, the cushioning effect may be reduced. Also injury can cause a disc to bulge and press on the nerve root leaving the spinal column, possibly causing extreme pain.

More specifically, when the outer wall of a disc, called the annulus fibrosus, becomes weakened through age or injury, it may tear allowing the soft inner part of the disc, the nucleus pulposus, to bulge out. This is called disc herniation, disc prolapse, or a slipped or bulging disc. Once the inner disc material extends out past the regular margin of the outer disc wall, it can press against very sensitive nerve tissue in the spine. The "bulging" disc can compress or even damage the nerve tissue, and this can cause weakness, tingling, or pain in the back area and into one or both legs.

In a surgical procedure known as a discectomy a surgeon may remove part of an intervertebral disc that is putting pressure on a nerve as it leaves the spinal column. The procedure is most commonly performed on lumbar discs (located in the lower back) where the patient experiences leg pain. However, the procedure may also be used for treating cervical discs in the neck.

Open discectomy is usually performed under general anesthesia (the patient is unconscious) and typically requires a one-day hospital stay. Discectomy typically proceeds while the patient lies face down or takes a kneeling position. During the procedure, the surgeon will make an approximate one-inch incision in the skin over the affected area of the spine. The surgeon removes muscle tissue from the bones above and below the affected disc while retractors hold the muscle and skin away from the surgical site to provide surgeon with a clear view of the vertebrae and disc. In some cases bone and ligaments may have to be removed for the surgeon to be able to visualize and then gain access to the bulging disc without damaging the nerve tissue, this is called a laminectomy or laminotomy depending on how much bone is removed.

Once the surgeon can visualize the vertebrae, disc and other surrounding structures, he or she will remove the section of the disc that is protruding from the disc wall and any other disc fragments that may have been expelled from the disc. This is often done under magnification. No material is used to replace the disc tissue that is removed. The incision is then closed with sutures and the patient is taken to a recovery room.

The most common problem of a discectomy is that there is a chance that another fragment of disc will herniate and cause similar symptoms down the road. This is a so-called recurrent disc herniation, and the risk of this occurring is about 10-15%.

The discectomy procedure described above is limited to the removal of the herniated portion of the disc. Another disc removal procedure is intended to treat the situation where the disc is damaged to the point that it must be removed and replaced. Typically, the disc is replaced by a cage that functions to fuse the vertebral bodies located above and below the disc. Depending on approach, such procedures are called either (1) TLIF or Transforaminal Lumbar Interbody Fusion, or (2) ALIF, that is, Anterior Lumbar Interbody fusion. Both approaches entail disc space preparation that includes steps of (1) facetectomy, bone removal for obtaining access to the disc space, (2) annulotomy, or cutting through the annulus to allow access to the disc space, (3) Nucleus Pulposus removal, (4) Annulus Fibeosus removal, and (5) endplate preparation, that is, removal of soft tissue from the superior and inferior vertebral body endplate to ensure cage-bone contact needed for fusion.

OBJECTS OF THE INVENTION

It is an object of the present invention to provide an improved approach for a discectomy procedure or a disc space preparation procedure.

Another object of the present invention is to provide a surgical discectomy method that is at least partially quicker and easier to carry out than conventional techniques.

Yet another object of the present invention is to provide a surgical discectomy method that may be carried out in a minimally invasive procedure.

These and other objects of the invention will be apparent from the drawings and descriptions herein. Although every object of the invention is attained in at least one embodiment of the invention, there is not necessarily any embodiment which attains all of the objects of the invention.

SUMMARY OF THE INVENTION

A surgical method in accordance with the present invention comprises providing a surgical instrument, apparatus or system including an elongate probe with a distal end having at least one egress or outlet port. The method comprises inserting a distal end portion of the elongate probe into a spinal disc space adjacent two spinal vertebrae, ejecting or streaming energy such as a laser beam or a plasma jet from the at least one egress or outlet port into spinal disc material in the spinal disc space, and subsequently removing the elongate probe from the spinal disc space.

A plasma jet instrument used in a method in accordance with the present invention effectively vaporizes tissue and other organic material. Concomitantly, a surgical method in accordance with the present invention may attain the same end result when the surgical procedure utilizes other instrumentation that works to vaporize biological tissue and other organic matter. For example, a laser may be used instead of a plasma jet instrument. Accordingly, the present invention contemplates (a) operating on a patient to obtain access to spinal tissues at a predetermined surgical site, (b) inserting an ablative instrument into the patient so that an operative tip or end effecter at a distal end of the instrument is disposed proximate the surgical site, and (c) activating the ablative instrument to deliver energy to tissues at the surgical site in a predetermined amount effective to vaporize tissue and other organic material at the surgical site at or in a spinal disc space.

The spinal disc space may be located (i) between the two spinal vertebrae or (ii) laterally thereof in the case of a bulging or protruding disc, of (ii) both laterally and in between the two vertebrae. In the case that the target spinal disc space is located only laterally of the two vertebrae, the procedure may consist only of ablating and removing the disc material projecting outside of the spinal column, laterally of the spinal vertebrae. Otherwise, the procedure may additionally include ablating and removing spinal disc material that is disposed between the two vertebrae.

Pursuant to a further feature of the present invention, the surgical method further comprises aspirating gas and detritus from a surgical site within the spinal disc space. This aspiration may be accomplished via a channel along the elongate probe, for instance, between a sheath and the probe or within a sheath wall. The aspiration channel is operatively connected at a proximal end of the instrument to a suction source. Preferably, a filter or impurity trap is provided in a suction line for capturing detritus, particles and gases removed from the surgical site via the aspiration channel of the probe.

Pursuant to another feature of the present invention, the surgical method further comprises flowing air into the spinal disc space. This infusion of clean or fresh air may be implemented through a dedicated channel or passageway along the elongate probe, for instance, between a sheath and the probe or within a sheath wall. The air conduction channel or passageway is operatively connected at a proximal end of the instrument to a pressurized air supply such as a fan or air pump.

Air flow into the confined disc space prevents the occurrence of a vacuum condition during the aspiration of gas and detritus. Therefore, the air inlet may also be at atmospheric pressure with the outlet connected to a vacuum source.

In accordance with another feature of the present invention, the method further comprises, prior to the inserting of the distal end of the elongate probe into the spinal disc space, operating the surgical instrument to direct a plasma jet towards a spinal disc in the spinal disc space (exemplarily towards an outer surface of the spinal disc) and, by operating the surgical instrument to direct the plasma jet towards the spinal disc, forming at least one incision in the spinal disc, thereby enabling the inserting of the distal end portion of the elongate probe into the spinal disc space. The inserting of the distal end portion of the elongate probe into the spinal disc space may then include inserting the distal end portion into the incision.

A surgical method in accordance with the present invention comprises conducting a surgical procedure (laminectomy) on a patient to enable access to a spinal disc space adjacent two spinal vertebrae, inserting a distal end portion of a plasma jet instrument into the spinal disc space, and operating the plasma jet instrument to ablate tissue and spinal disc material in the spinal disc space. As indicated above, the spinal disc space and thus the ablation procedure may occur laterally of the two spinal vertebrae, in the case of a bulging disc, or between the two vertebrae, for instance, in the case of a nucleotomy.

Prior to the inserting of the distal end portion of the plasma jet instrument into the spinal disc space, one may operate the plasma jet instrument to direct a plasma jet towards an outer surface of a spinal disc in the spinal disc space between the adjacent spinal vertebrae and thereby form at least one incision in the spinal disc, to enable insertion of the distal end portion of a plasma jet instrument into the spinal disc space.

Pursuant to a supplemental feature of the present invention, the surgical method may further entail operating a scanning apparatus to obtain 3D structural data pertaining to organic structures at a contemplated surgical site in the patient, that is, in a region including the spinal disc and the adjacent vertebrae. The scanning of the patient may occur prior to the surgical procedure, with the structural information being stored in a computer memory for display on a video or computer monitor during the spinal disc ablation procedure. The inserting of the distal end portion of the plasma jet instrument is then advantageously guided or directed in accordance with the structural data.

The present invention additionally contemplates automatically tracking a position of the plasma jet instrument during inserting of a distal end portion thereof into the spinal disk space, comparing a position of the distal end portion in real time with the 3D structural data, and directing movement and activation of the plasma jet instrument in accordance with the position of the distal end portion in real time and with the 3D structural data. The comparing of the position data and controlling the movement and activation of the plasma jet instrument may be undertaken manually, exemplarily under visual observation of the structures as imaged on a video monitor, or may be implemented by a robotic system.

According to yet another feature of the present invention, the surgical method further comprises transmitting waveform energy (e.g., light, via an optical fiber or cable) into the patient in a region about the contemplated surgical site. The inserting of the distal end portion of the plasma jet instrument then includes guiding or directing the distal end portion of the plasma jet instrument in accordance with organic structural information obtained in response to directing of the waveform energy into the patient.

A surgical device in accordance with the present invention comprises an elongate instrument having at least two channels or lumens. A first one of the channels or lumens is operatively connectable to a source of pressurized plasma gas while a second one of the channels or lumens is operatively couplable to a source of vacuum underpressure or suction. A filter or trap may be provided in a line to the vacuum or suction source for extracting debris, toxins, gases, etc. The elongate instrument of the surgical device may include a third channel or lumen configured to conduct air to a distal end of the elongate instrument for infusing an surgical site with air.

The elongate instrument may include an elongate probe or shaft that is steerable. More specifically, the elongate probe or shaft has a distal end portion that is flexible. Mechanical elements such as tension wires or piezoelectric actuators are disposed in physical contact or operative engagement with the distal end portion of the probe or shaft and configured to bend or turn the distal end portion.

In an alternative embodiment of the instrument, an elongate probe or shaft of the instrument has a distal end portion provided with a first egress or output port for directing plasma energy in a distal or forward direction, parallel to a longitudinal axis of the elongate shaft or probe. The distal end portion of the elongate probe or shaft is further provided with a second egress or output port for directing plasma energy in a lateral direction, transverse to the longitudinal axis of the elongate shaft or probe.

Probe steering or a laterally directed plasma jet facilitate control of disc ablation, to shape the disc material as desired.

The surgical device may further comprise a scanning apparatus for monitoring 3D structure of organic tissues of the patient, a position feedback system operatively connected to the elongate instrument to automatically continuously monitor position and optionally orientation of the elongate instrument, and comparison componentry operatively connected to the scanning apparatus and the position feedback system to enable proper positioning of the elongate instrument relative to the organic tissues of the patient. The comparison componentry may take the form of a video monitor enabling the surgeon to undertake the comparison or, alternatively, may include robot software that controls instrument positioning and activation in accordance with relative positions of instrument and internal organic structures of the patient.

BRIEF DESCRIPTION OF THE DRAWINGS

FIG. 2 is partially a schematic side perspective view of a probe with a navigation array for tracking the position of the probe and enabling at least partially automatic control of probe positioning and activation relative to internal organic spinal structures of a patient; FIG. 2 is also partially a block diagram showing functional units of a signal processing system for monitoring position and orientation of the probe and controlling probe position and activation.

DETAILED DESCRIPTION

Figure 1:
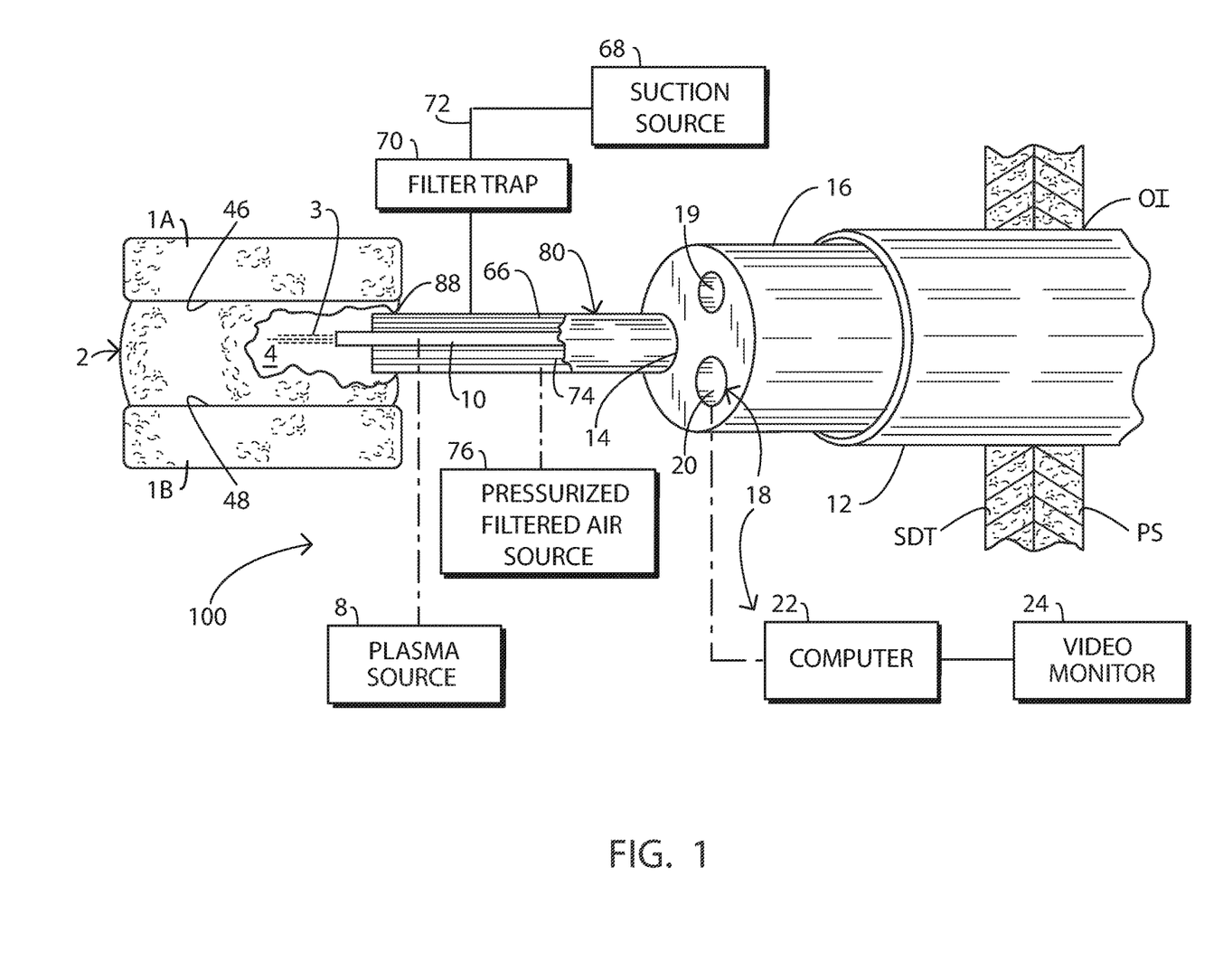
FIG. 1 is a schematic perspective view of a plasma jet instrument pursuant to the present invention inserted into a spinal disc space between two spinal vertebrae for carrying out a procedure in accordance with the invention.

As illustrated in FIG. 1, a surgical instrument assembly 100 includes a plasma jet probe 10 that ejects a plasma jet 3 for use in spinal surgery to ablate spinal disc material 4 in a spinal disc space 2 between two adjacent vertebrae 1A and 1B. Probe 10 includes a channel or lumen 6 (see FIGS. 3 and 4) operatively connected at a proximal end to a source 8 of plasma. Any medically safe and effective plasma can be used, for instance, argon plasma. A distal end portion (not separately designated) of the probe 10 may be introduced proximate to the spinal disc space 2 via an open incision OI in a patient's skin PS and sub-dermal tissues SDT and optionally via a laparoscopic cannula 12 and/or a working channel 14 of an endoscope 16.

Visualization of the surgical site may be obtained in the case of an open incision via direct inspection or in the case of a laparoscopic or endoscopic procedure via a conventional endoscopic or laparoscopic optical viewing system 18 including illumination optics 19, a CCD camera 20, a computer 22 operatively connected to the camera, and a video monitor 24. Computer 22 operates under known digital processing software to convert CCD signals into an image displayed on video monitor 24.

Figure 2:
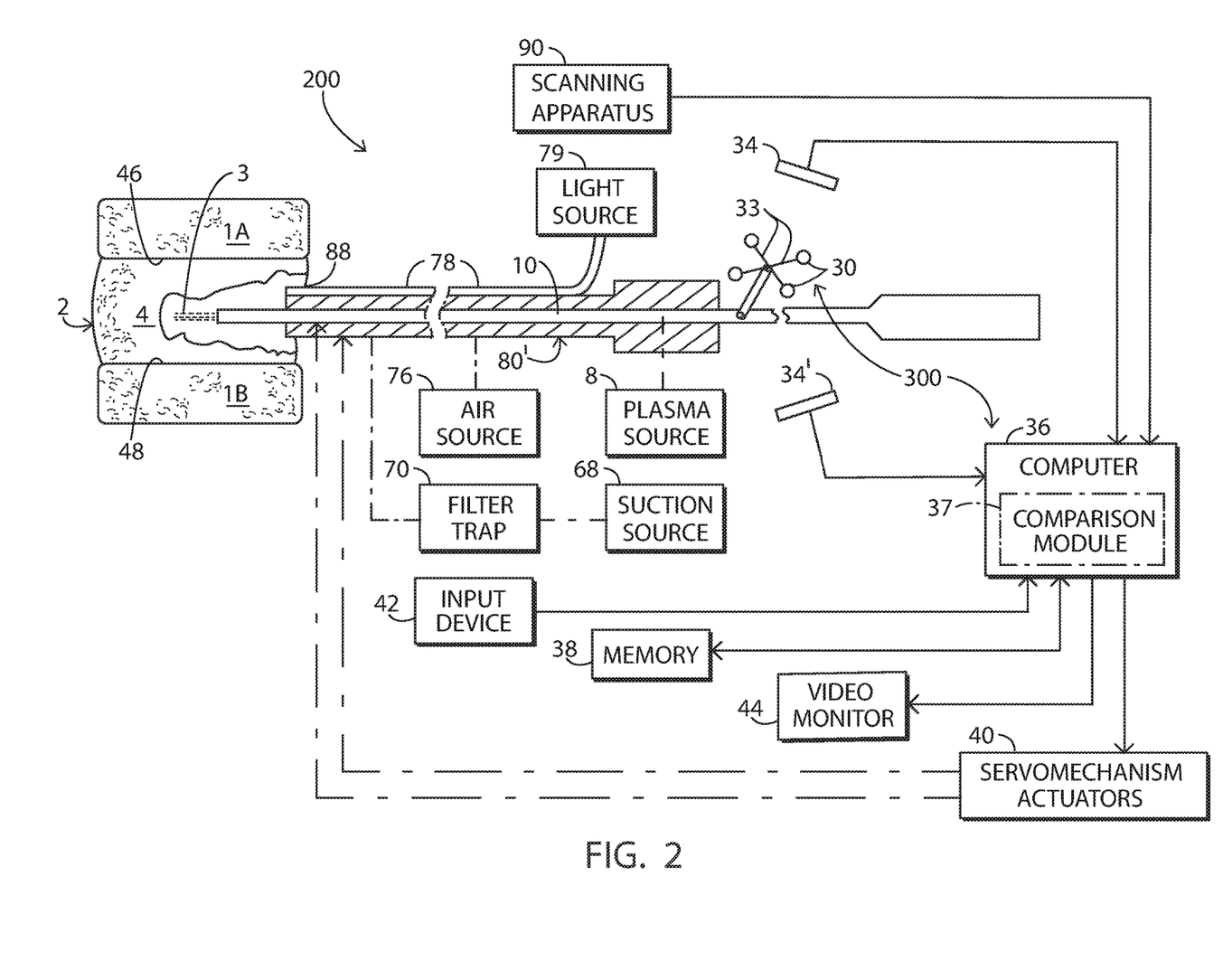

Alternatively, as in a surgical system 200 depicted in FIG. 2, a navigation array 26 comprising a plurality of radio-opaque or MRI detectible markers (not shown) or optically visible elements 30 detectible via an optical or video system 32 may be used to monitor the position and orientation of the plasma jet probe 10 in real-time. Navigation array 26 is rigidly connected to plasma jet probe 10 and includes, for instance, a plurality of spokes 33 holding optically detectable exemplarily spherical or cubical elements 30 whose locations are picked up preferably by video system 32. This allows referencing the information related to instrument location to that of the patient's anatomy. Prior to the surgery a similar array is connected to the patient body and used to acquire anatomical data in a pre-scan procedure conducted with a scanning apparatus 90, whether an MRI apparatus, a CAT scanner, a camera system (34, 34'), or possibly ultrasound. In this manner, the instrument location can be linked directly to the patient. Video system 32 includes at least one and preferably a plurality of video cameras 34, 34' (e.g., charge coupled devices) disposed at mutually spaced locations about an operating room table (not shown) and operatively connected to a computer 36 with software-implemented image processing functionality. Computer 36 is connected to a video monitor 44 for displaying images to inform surgeons and other operating room personnel. In addition, computer 36 may execute software-realized control of probe 10 during a surgical procedure. To that end, computer 36 is operatively connected to (i) a memory 38 containing organic structural information obtained during a pre-operative patient scan and (ii) a robotic servomechanism 40 including actuators such as articulated armatures, electric motors, position encoders, hydraulic cylinders, etc. Computer 36 receives scan data from apparatus 90 and stores patient structural information in memory 38. Computer 36 includes comparison circuitry or functionality 37 for comparing probe position and orientation information from navigation system 26 with patient anatomy stored in digitized form in memory 38. Computer 36 selectively energizes robot actuators 40 to change the position and orientation of probe 10 preferably partially in response to operator instructions entered via an input device 42 such as a mouse, keyboard, touchpad, or joystick. Memory 38, actuators 40 input device 42, and scanning apparatus 90 may be included in the system of FIG. 1 as well, for controlling probe 10 thereof partially separately from movements of endoscope 16.

The position and orientation of probe 10 may be displayed on video monitor 24 or 44 together with previously recorded structures (stored in memory, e.g., memory 38) of the internal organs of the patient at the surgical site, including vertebrae 1A and 1B flanking and defining the spinal disc space 2, thereby enabling a surgeon to manipulate the probe relative to the organic structures and activate the instrument to direct plasma jet 3 to ablate disc material, and optionally cauterize, tissue and organic material.

Figure 3:
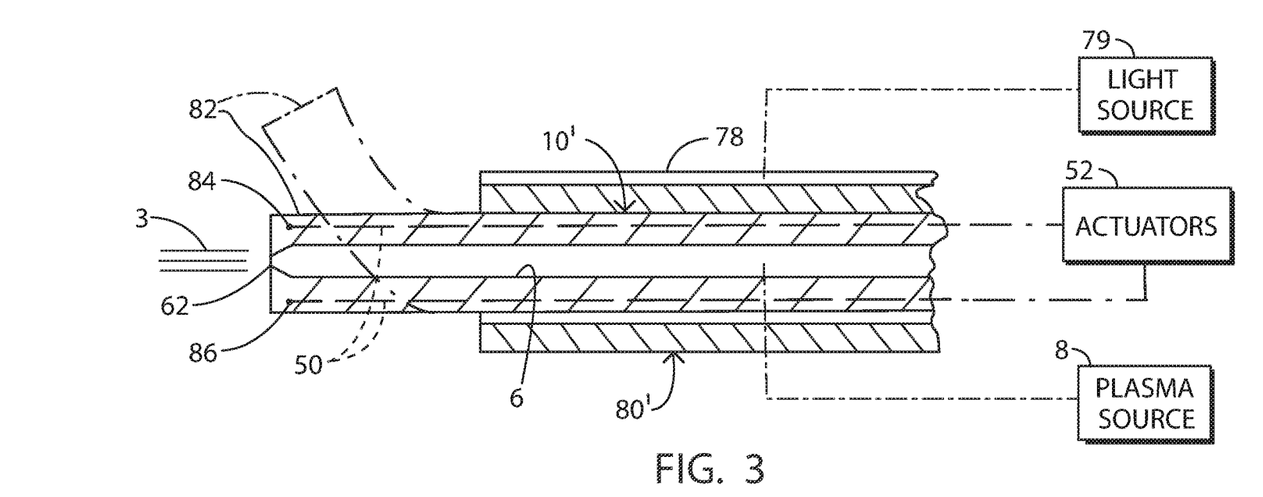
FIG. 3 is a schematic side elevational view of a steerable plasma jet probe utilizable with processing and control functional apparatus of FIG. 2 for use in performing a surgical procedure in accordance with the present invention.

Pursuant to FIG. 3, the surgeon may also turn a flexibly configured distal end 82 of a plasma jet probe 10' to laterally direct ejected plasma jet 3 alternately towards vertebra 1A and 1B and inwardly facing surfaces 46 and 48 thereof (see FIGS. 1, 2, and 4) to clean and prepare the surfaces for receiving a prosthetic insert (not shown) in the spinal disc space 2. To that end plasma jet probe 10' may be provided with mechanical elements for effectuating directional control, such as wires or cables 50 such as those exhibited by steerable catheters. Distal ends of wires or cables 50 are connected at 84, 86 to the distal end of probe 10 while proximal ends (not labeled) of wires or cables 50 are operatively coupled to actuators 52 activated by computer 24 or 36 pursuant to instructions provided by a surgeon via input device 42 or in accordance with a pre-programmed surgical procedure. Probe 10 of FIGS. 1 and 2 may be provided with the steering or direction control of probe 10'.

Figure 4:
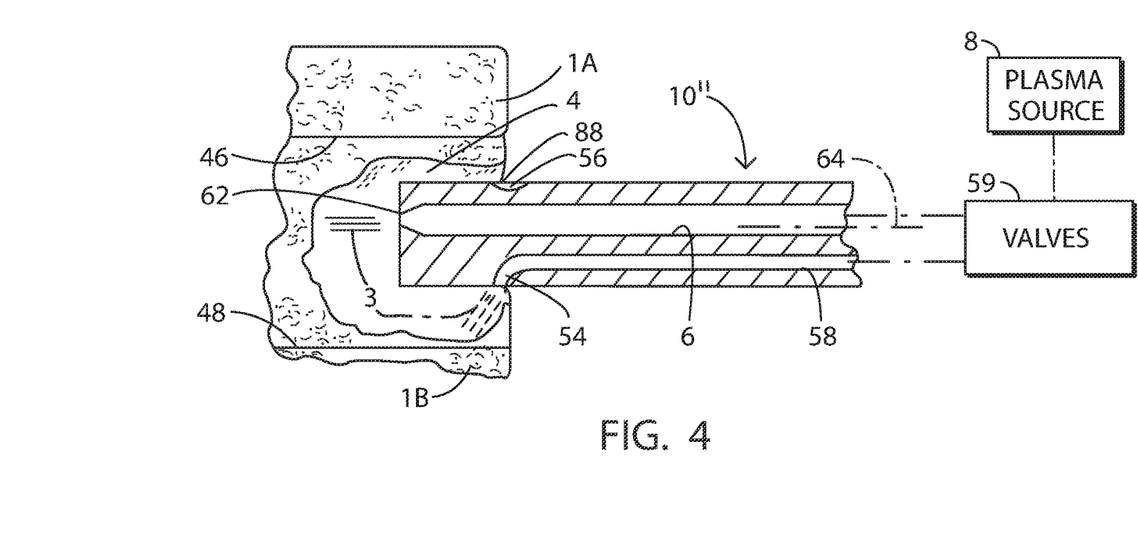
FIG. 4 depicts a plasma jet probe with a distally directed gas outlet and a laterally directed plasma outlet for use in performing a surgical procedure in accordance with the present invention.

The same sideways directional control or orienting of plasma jet 3 may be alternatively accomplished by providing one or two lateral outlets or openings 54 and 56 at the distal end of a plasma jet probe 10", as illustrated in FIG. 4. In the event of a single lateral opening 54, probe 10" may be rotated about its longitudinal axis 64 to direct the plasma jet 3 alternately towards one vertebral surface 46 or the other 48. In the case of two or more lateral openings 54, 56 and a single lumen or channel 6, probe 10" may be provided at a distal end with one or more gates (not shown). Alternatively or additionally, probe 10" may have multiple plasma guidance conduits or lumens 6 and 58 used to separately convey plasma jet material to a distal end orifice 62 and to lateral outlets 54 and 56, respectively, in accordance with an actuation configuration of a valve set and manifold 59.

It is contemplated to use the plasma jet instrument and probe 10, 10', 10" in a discectomy procedure. Such a procedure involves removing at least a portion of a spinal lamina to form an access path in a patient. This laminectomy is adapted to, and utilizes techniques consistent with, the mode of access, that is, open, laparoscopic, or endoscopic. The surgeon inserts the plasma jet instrument and particularly a distal end portion of the probe 10 along the access path so that a distal tip of the instrument is positioned near spinal disc material 4 in spinal disc space 2. That space, in the case of a bulging or herniated disc, occupies at least in part a lateral position adjacent to and outside the two vertebrae 1A and 1B. The plasma jet instrument is operated to direct plasma jet 3 in a desired direction towards the spinal disc material 4 in the spinal disc space 2 to ablate the disc material as necessary.

The elongate probe 10 of plasma jet instrument assembly 100 has at least one egress or outlet port or orifice 62 at the distal end (see FIGS. 3 and 4). FIG. 4 shows three jet ejection ports 54, 56, and 62. A plasma jet 3 may be emitted from lateral port 54 or 56 of probe 10" largely perpendicular to longitudinal axis 64, or through distal end port 62 in a distal direction parallel to axis 64.

The distal end portion of probe 10, 10', or 10" may be inserted into spinal disc space 2 beside and between spinal vertebrae 1A and 1B, with plasma jet 3 streaming from egress or outlet port 62 (or 54, 56) into spinal disc material 4 in the spinal disc space 2. Subsequently, upon completion of a discectomy or ablation procedure, probe 10, 10', 10" is removed from the spinal disc space 2.

The method also contemplates removal of bulging or protruding spinal disc material 4 located outside of spinal disc space 2 between vertebrae 1A and 1B, in the case of a herniated disc. The procedure may additionally include ablating and removing spinal disc material 4 disposed between the two vertebrae 1A and 1B.

The surgical method further comprises aspirating gas and detritus from the surgical site within the spinal disc space 2. As illustrated in FIG. 1, this aspiration may be accomplished via a channel 66 preferably disposed alongside probe 10, for instance, between a sheath 80 and the probe or within a sheath wall. Aspiration channel 66 is operatively connected at a proximal end of the instrument to a suction source 68. Preferably, a filter or impurity trap 70 is provided in a suction line 72 for capturing detritus, particles and gases removed from the spinal disc space 2 via aspiration channel 66.

The surgical method may further comprise flowing air into the spinal disc space 2. As indicated in FIG. 1, this infusion of clean, filtered fresh air may be implemented through a dedicated channel or passageway 74 in sheath 80 or between the sheath and probe 10 or within a sheath wall. The air conduction channel or passageway 74 is operatively connected at a proximal end of the instrument to a pressurized air supply 76 such as a fan or air pump.

The method may entail forming an initial incision 88 (FIGS. 1, 2, and 4) into disc material 4 in spinal disc space 2, with the plasma jet probe being then inserted into or through the incision to operate further on the spinal disc material 4 in disc space 2. More specifically, prior to the inserting of the distal end of the elongate probe into the spinal disc space 2, one operates the surgical instrument to direct plasma jet 3 towards spinal disc material 4 in the spinal disc space 2 (exemplarily towards an outer surface of a spinal disc) and, by operating the surgical instrument to direct the plasma jet 3 towards the spinal disc, forming at least one incision 88 in the spinal disc. The inserting of the distal end portion of the elongate probe 10 into spinal disc space 2 may then include inserting the distal end portion of the probe into and through the incision 88.

As discussed above, the position and orientation of the plasma jet probe 10, 10', 10" may be automatically tracked during inserting of a distal end portion thereof into the spinal disk space 2. A position (and optionally orientation) of the distal end portion in real time is compared with the 3D structural data, so that the movement and activation of the plasma jet instrument may be controlled in accordance with the position of the distal end portion in real time and with the 3D structural data. The comparing of the position data and controlling the movement and activation of the plasma jet instrument may be undertaken manually, exemplarily under visual observation of the structures as imaged on a video monitor, or may be implemented by a robotic system. In the latter case, the plasma jet instrument is mounted to an electromechanical servomechanism with actuators 40 (FIG. 2) controlled by a computer to manipulate the probe 10, 10', 10" pursuant to a preprogrammed protocol and/or in response to instructions input by a surgeon during the spinal disc ablation procedure. The plasma jet 3 may be directed in part to remove material adhering to inwardly facing surfaces 46, 48 of spinal vertebrae 1A, 1B. (See FIGS. 3 and 4.)

A surgical method utilizing the apparatus disclosed herein contemplates the transmitting of waveform energy (e.g., light, via illumination optics 19, FIG. 1, or an optical fiber or fiber bundle 78, FIGS. 2 and 4, connected to a light source 79) into the patient in a region about the contemplated surgical site. The inserting of the distal end portion of the plasma jet probe 10, 10', 10" then includes guiding or directing the distal end portion of the probe in accordance with organic structural information obtained in response to directing of the waveform energy into the patient.

Plasma jet instrument assembly 100, 200 as contemplated herein comprises cooperating components including elongate probe 10, 10', 10" and a sheath 80 or 80' (FIGS. 2 and 3) having at least two channels or lumens 6, 66 (see FIG. 1). Channel or lumen 6 is operatively connectable to source 8 of pressurized plasma gas while channel or lumen 66 is operatively couplable to a source 68 of vacuum underpressure or suction. Channel or lumen 74 is optional and configured to conduct air to a distal end of probe 10 for infusing an surgical site with air. Sheath 80' in FIGS. 2 and 3 includes optical fiber 78 connected to light source 79, while illumination in plasma jet instrument assembly 100 of FIG. 1 is provided by endoscope optics 19. Sheath 80' (also utilizable with probe 10" of FIG. 4) may be further provided with optics such as a fiber optic cable or a CCD camera connected to signal processing apparatus such as a computer for providing visual feedback via a video monitor (none shown).

A surgical system may include plasma jet instrument assembly 100, 200, as well as a position feedback apparatus or system including navigation array 26 connected to probe 10 and cameras 34, 34' for automatically and continuously monitoring position and optionally orientation of the probe 10, 10', 10". This position feedback apparatus is preferably connected to computer 22, 36 which stores structural information in memory 38 as to the patient's spinal structures at the preselected surgical site, the information being stored as a result or a previous scan or by a contemporaneous scan by a scanning apparatus for monitoring 3D structure of organic tissues of the patient. Computer 22, 36 may be configured to compare the real-time position of the plasma jet probe with the organic structural information to enable proper positioning of the elongate instrument relative to the organic tissues of the patient, either automatically via a robotic apparatus or manually by the attending surgeon. In the latter case, the comparison is undertaken with the aid of video monitor 24, 44.

Plasma jet instrument assembly 100, 200 is registered prior to use by placing it in a fixture that allows for precise calculation of the exit point location of plasma jet 3. Also for the steerable instrument (FIG. 3), the curvature of the distal end is induced in incremental steps by pulling a trigger or rotating a dial. Once this is registered the instrument is used its curved configuration.

Assembly or system 100, 200 may include robotic servomechanism actuators 40 operatively connected to probe 10, 10', 10" or another tissue vaporization instrument such as a laser probe, for automatically moving the instrument, scanning apparatus 300 including navigation array 26 for monitoring position and optionally orientation of probe 10 relative to internal tissue structures of a patient, and computer 36 operatively connected to the robotic servomechanism 40 and the scanning apparatus 300 for actuating and controlling the robotic servomechanism to maneuver tissue-vaporization plasma jet probe 10, 10', 10" in accordance with position and optionally orientation of elongate instrument relative to the internal tissue structures of the patient at the surgical site.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A surgical method comprising:
   providing a surgical instrument including an elongate probe with a distal end having at least one egress or outlet port;
   inserting a distal end portion of said elongate probe into a spinal disc space adjacent two spinal vertebrae;
   generating plasma outside of the spinal disc space;
   conducting the plasma through said elongate probe;
   emitting or ejecting the plasma as a plasma jet from said at least one egress or outlet port into spinal disc material in said spinal disc space in a predetermined amount effective to vaporize tissue and other organic material at the surgical site at or in a spinal disc space; and
   subsequently removing said elongate probe from said spinal disc space.

2. The surgical method defined in claim 1, further comprising aspirating gas and detritus from a surgical site within said spinal disc space.

3. The surgical method defined in claim 2, further comprising flowing air into said spinal disc space.

4. A surgical method comprising:
   providing a surgical instrument including an elongate probe with a distal end having at least one egress or outlet port;
   inserting a distal end portion of said elongate probe into a spinal disc adjacent two spinal vertebrae;
   prior to the inserting of said distal end portion of said elongate probe into said spinal disc, operating said surgical instrument to direct a plasma jet towards an outer surface of the spinal disc;
   by operating said surgical instrument to direct said plasma jet towards the spinal disc, forming at least one incision in said spinal disc, thereby enabling the inserting of said distal end portion of said elongate probe into said spinal disc;
   after the inserting of said distal end portion of said elongate probe into the spinal disc, emitting or ejecting the plasma from said at least one egress or outlet port into spinal disc material between said two spinal vertebrae in a predetermined amount effective to vaporize tissue and other organic material at the surgical site at or in a spinal disc space; and
   subsequently removing said elongate probe from said spinal disc.

5. The surgical method defined in claim 4, wherein the inserting of said distal end portion of said elongate probe into said spinal disc space includes inserting said distal end portion into said incision.

6. The surgical method defined in claim 4 wherein the operating of said surgical instrument to direct said plasma jet towards said spinal disc includes directing said plasma jet towards an outer surface of said spinal disc, and wherein the inserting of said distal end portion of a plasma jet instrument into said spinal disc space includes inserting said distal end portion of said elongate probe into said incision.

7. A surgical method comprising:
   conducting a surgical procedure on a patient to enable access to a spinal disc space adjacent two spinal vertebrae;
   inserting a distal end portion of a plasma jet instrument into the spinal disc space;
   generating plasma outside of the spinal disc space;
   after the inserting of said distal end portion of said plasma jet instrument into said spinal disc space, conducting the plasma through said plasma jet instrument; and
   operating said plasma jet instrument to direct the plasma as a jet stream toward tissue and spinal disc material in said spinal disc space to thereby ablate the tissue and spinal disc material.

8. The surgical method defined in claim 7, further comprising operating a scanning apparatus to obtain 3D structural data pertaining to organic structures at a contemplated surgical site in the patient, the inserting of said distal end portion of said plasma jet instrument being guided or directed in accordance with said structural data.

9. The surgical method defined in claim 8, further comprising:
   automatically tracking a position of said plasma jet instrument during inserting of a distal end portion thereof into the spinal disc space;
   comparing a position of said distal end portion in real time with the 3D structural data; and
   directing movement and activation of said plasma jet instrument in accordance with the position of said distal end portion in real time and with the 3D structural data.

10. The surgical method defined in claim 7, further comprising transmitting waveform energy into the patient in a region about said contemplated surgical site, the inserting of said distal end portion of said plasma jet instrument including guiding or directing said distal end portion of said plasma jet instrument in accordance with organic structural information obtained in response to directing of the waveform energy into the patient.

11. The surgical method defined in claim 7, further comprising aspirating gas and detritus from said spinal disc space.

12. The surgical method defined in claim 7, further comprising flowing air into said spinal disc space.

13. A surgical method comprising:
- conducting a surgical procedure on a patient to enable access to a spinal disc space adjacent two spinal vertebrae;
- inserting a distal end portion of a plasma jet instrument into the spinal disc space;
- prior to the inserting of said distal end portion of said plasma jet instrument into said spinal disc space, operating said plasma jet instrument to direct a plasma jet towards an outer surface of a spinal disc in said spinal disc space between said adjacent spinal vertebrae;
- by the operating of said plasma jet instrument to direct said plasma jet towards said outer surface of said spinal disc, forming at least one incision in said spinal disc, thereby enabling the inserting of said distal end portion of a plasma jet instrument into said spinal disc space; and
- operating said plasma jet instrument to ablate tissue and spinal disc material in said spinal disc space.

* * * * *